(12) United States Patent
Yamagishi

(10) Patent No.: US 10,242,161 B2
(45) Date of Patent: Mar. 26, 2019

(54) AUTOMATIC DRUG DISPENSING AND PICKING SYTEM

(71) Applicant: JB-Create, Inc., Ishikawa (JP)

(72) Inventor: Juro Yamagishi, Ishikawa (JP)

(73) Assignee: JB-Create, Inc., Ishikawa (JP)

( * ) Notice: Subject to any disclaimer, the term of this patent is extended or adjusted under 35 U.S.C. 154(b) by 265 days.

(21) Appl. No.: 15/460,257

(22) Filed: Mar. 16, 2017

(65) Prior Publication Data

US 2018/0268112 A1    Sep. 20, 2018

(51) Int. Cl.
*G06F 19/00* (2018.01)
*G07F 17/00* (2006.01)

(52) U.S. Cl.
CPC ...... *G06F 19/3462* (2013.01); *G07F 17/0092* (2013.01)

(58) Field of Classification Search
CPC .................................................. G07F 17/0092
See application file for complete search history.

(56) References Cited

U.S. PATENT DOCUMENTS

| 5,502,944 A * | 4/1996 | Kraft ................... G07F 17/0092 |
| | | 53/55 |
| 6,006,946 A * | 12/1999 | Williams .............. B65G 1/045 |
| | | 221/2 |
| 2005/0035138 A1 * | 2/2005 | Guerra .................. B65G 1/04 |
| | | 221/123 |
| 2010/0300041 A1 * | 12/2010 | Kim ...................... G07F 11/165 |
| | | 53/281 |

FOREIGN PATENT DOCUMENTS

| JP | H10-192368 A | 7/1998 |
| JP | 2013-226182 A | 11/2013 |
| JP | 2004-275550 A | 10/2014 |

* cited by examiner

*Primary Examiner* — Timothy R Waggoner
(74) *Attorney, Agent, or Firm* — Nakanishi IP Associates, LLC

(57) ABSTRACT

An automatic drug dispensing and picking system that automatically dispenses prescribed drugs on the basis of prescription data includes a plurality of drug bottle storage racks storing a plurality of drug bottles, a traveling rail, a crane device, a drug bottle control device, a cap removing device, a drug picking device. The drug bottle is stored in the corresponding drug bottle storage rack with each drug bottle laid horizontally. The crane device includes a picking arm and pick the drug bottle from the corresponding one of the drug bottle storage racks. The drug bottle control device includes a drug bottle holding section, a sliding section capable of sliding the drug bottle holding section, a drug bottle turning section configured to turn the drug bottle holding section vertically at a predetermined angle, a drug bottle raising and lowering section configured to raise and lower the drug bottle holding section.

15 Claims, 16 Drawing Sheets

AUTOMATIC DRUG DISPENSING AND PICKING SYTEM

BACKGROUND

Technical Field

The present invention relates to an automatic drug dispensing and picking system that automatically dispenses, on the basis of prescription data, drugs contained in a drug bottle stored in a drug bottle storage rack.

Related Art

As a conventional drug dispensing method, for example, a person in charge of dispensing drugs moves toward a drug bottle storage rack. On the basis of provided prescription data, the person in charge searches the drug bottle storage rack for a drug bottle containing drugs to be dispensed, and then takes the drug bottle out therefrom. Subsequently, from the drug bottle taken out, the person in charge takes out the number of drugs necessary for the prescription, and then hands the drugs to a patient in a prescription bag. With this method, however, dispensing work is time-consuming. Furthermore, there is an issue of dispensing incorrect drugs due to human error. Such a drug dispensing error occurs with a certain probability.

In general, drug bottles are stored in an upright position on each shelf of a drug bottle storage rack. However, it is pointed out that such a storage method takes up space, making it difficult to automate prescription and dispensing work. Accordingly, for example, automatic drug dispensers are in use as disclosed in JP 2004-275550 A and JP 10-192368 A. Prior to dispensing drugs with such an automatic drug dispenser, the drugs are taken out from a drug bottle, and then put and stored in a dedicated cassette case. When the drugs need to be dispensed, a person in charge of dispensing drugs causes a machine in the automatic drug dispenser to automatically take out the drugs inside the cassette case.

With such an automatic drug dispenser, however, drugs need to be taken out from a drug bottle and put into a dedicated cassette case in advance. Therefore, the issues of such complicated drug replacement work and the mixing of different drug lots may arise. Furthermore, since there is a limited number of cassette cases available, automation of dispensing that supports numerous drugs is considered to be difficult.

In general, out of approximately 2,000 kinds of drugs stored in a pharmacy or the like, as little as approximately 10% to 20% of drugs that are often prescribed are dispensed. In addition, inventory management is less than perfect in typical pharmacies because drug bottles are simply stored in a drug bottle storage rack provided in a floor space.

Furthermore, devices and systems capable of automatically picking and discharging medicines are recently being developed and introduced, in order to improve the efficiency of the medicine picking work. For example, JP 2013-226182 A discloses a drug dispensing system that includes a prescription data input device, a drug discharging device, and a picking inspection device. The prescription data input device allows prescription data to be input on the basis of a prescription. The drug discharging device discharges, on the basis of the prescription data, drugs contained in the system in advance. The picking inspection device subjects the drugs picked in accordance with the prescription data to a picking inspection.

As described above, in conventional dispensing work for prescription, there is a possibility that a dispensing error occurs due to human error, causing an issue of dispensing and providing incorrect drugs. Furthermore, since stocktaking is carried out by a human operator, inventory management tends to be unsatisfactory.

Furthermore, as described above, in the automatic drug dispensers disclosed in JP 2004-275550 A and JP 10-192368 A, the issues of complicated drug replacement work and the mixing of different drug lots may occur. In addition, since there is a limited number of cassette cases available, supporting numerous drugs is difficult.

In the system disclosed in JP 2013-226182 A, the items of medicines that can be automated are top hundreds of items, and supporting these items may increase the cost of the device itself. As a result, it is considered extremely difficult to support and operate all the medical items stocked in a hospital or dispensing pharmacy.

SUMMARY

The present invention has been made to solve these issues. An object of the present invention is to provide an automatic drug dispensing and picking system that allows numerous drugs to be stored even in a limited space such as a dispensing pharmacy, allows prescribed drugs to be automatically dispensed at high speed, reduces human error, and improves inventory management.

According to an embodiment of the present invention, the following technical means are adopted to solve the issues described above.

An automatic drug dispensing and picking system that automatically dispenses prescribed drugs on the basis of prescription data, the automatic drug dispensing and picking system including:

a plurality of drug bottle storage racks arranged side by side in parallel at a predetermined interval, each drug bottle storage rack including multiple shelves and rows and storing a plurality of drug bottles, each drug bottle containing drugs therein and including a cap attached thereto;

a traveling rail arranged between, and along a width direction of, the drug bottle storage racks arranged side by side;

a crane device configured to travel the traveling rail and pick, on the basis of the prescription data, a drug bottle containing the prescribed drugs from a corresponding one of the drug bottle storage racks;

a drug bottle control device configured to receive, from the crane device, the drug bottle that the crane device has picked from the corresponding drug bottle storage rack, and discharge, from the received drug bottle, the drugs contained therein to an adjacent tray;

a cap removing device configured to remove a cap attached to the drug bottle that the drug bottle control device has received from the crane device; and a drug picking device configured to pick, from among the drugs discharged to the tray by the drug bottle control device, the number of drugs necessary for prescription on the basis of the prescription data, and put the picked drugs into a prescription bottle conveyed by an adjacent conveyance belt, wherein each drug bottle is stored in the corresponding drug bottle storage rack with each drug bottle laid horizontally in a direction in which the cap attached thereto faces the traveling rail, wherein the crane device includes a picking arm attached thereto and configured to be driven to rotate in a horizontal direction, and causes the picking arm to grasp the cap of the drug bottle to pick the drug bottle from the corresponding one of the drug bottle storage racks arranged on both sides of the crane device, and then pass the drug bottle to the drug bottle control device, while maintaining the state of the drug bottle laid horizontally, the drug bottle control device includes a drug bottle holding section configured to grasp and hold, from an outside of the drug bottle, the drug bottle received from the crane device, a sliding section capable of sliding the drug bottle holding section toward and away from the tray, a drug bottle turning section configured to turn the drug bottle holding section vertically at a predetermined angle, and a drug bottle raising and lowering section configured to raise and lower the drug bottle holding section within a predetermined height range, in discharging the drugs contained in the drug bottle to the tray, the sliding section slides, toward the tray, the drug bottle holding section grasping the drug bottle received from the crane device, the drug bottle turning section vertically turns the drug bottle holding section such that the cap attached to the drug bottle faces upward, the cap removing device removes the cap attached to the drug bottle to expose an opening portion of the drug bottle, the drug bottle turning section discharges the drugs contained in the drug bottle to the tray by turning the drug bottle holding section vertically at the predetermined angle, and the drug bottle turning section vertically turns the drug bottle holding section such that the opening portion of the drug bottle faces upward, in containing, among the drugs discharged to the tray, drugs unnecessary for the prescription again in the drug bottle, the drug bottle raising and lowering section lowers the sliding section until the opening portion of the drug bottle is in a position near a height of the tray, the drug picking device puts the drugs unnecessary for the prescription from the tray into the opening portion of the drug bottle, the drug bottle raising and lowering section raises the sliding section until the drug bottle is in an initial height position, the cap removing device attaches the cap to the drug bottle again, the drug bottle turning section turns the drug bottle holding section vertically in the direction in which the cap attached to the drug bottle faces the traveling rail, and the sliding section slides the drug bottle holding section toward the traveling rail, and in storing the drug bottle in the corresponding drug bottle storage rack again, the drug bottle control device detaches the drug bottle holding section from the drug bottle and passes the drug bottle to the crane device, and the crane device stores, upon receiving the drug bottle from the drug bottle control device, the drug bottle in the corresponding one of the drug bottle storage racks arranged on both sides of the crane device by causing the picking arm to grasp the cap of the drug bottle while maintaining the state of the drug bottle laid horizontally.

According to an embodiment of the present invention, it is possible to store numerous drugs even in a limited space such as a pharmacy since drug bottles are stored horizontally in a drug bottle storage rack. Furthermore, by storing the drug bottles with their caps aligned, a crane device can pick the drug bottles easily, leading to improved work efficiency and work speed.

In addition, since the crane device picks a drug bottle itself for prescription, the work such as putting drugs in a cassette case is not necessary. Therefore, human error can be reduced. Furthermore, the mixing of different drug lots can be reduced. Furthermore, since dispensing work can be automated, the possibility of the dispensing errors such as providing incorrect drugs to a patient can be minimized.

Furthermore, since the crane device is used to pick and store drug bottles, it is possible to support numerous drugs with the use of a drug bottle storage rack having a height not reachable by a person. In addition, with a dispensing device, dispensing based on prescription data can be performed with improved accuracy.

BRIEF DESCRIPTION OF DRAWINGS

FIG. 1A is a schematic plan view of a configuration thereof; FIG. 1B is an enlarged schematic plan view of a configuration of a downstream portion from a drug bottle control device;

FIG. 2A is a schematic side view of the configuration thereof; FIG. 2B is an enlarged schematic side view of the configuration of the downstream portion from the drug bottle control device;

FIG. 3A is a schematic front view of the configuration thereof; FIG. 3B is an enlarged schematic front view of the configuration of the downstream portion from the drug bottle control device;

FIG. 4A is a view illustrating a state in which the drug bottle control device has received a drug bottle; FIG. 4B is a view illustrating a state in which the drug bottle has been slid toward a tray; FIG. 4C is a view illustrating the cap removing device removing a cap of the drug bottle; FIG. 4D is a view illustrating a state in which the cap has been removed by the cap removing device; FIG. 4E is a view illustrating a state in which the drug bottle is turned and drugs are being discharged to the tray by a drug bottle turning section;

FIG. 5A is a view illustrating a state in which the drug picking device is picking the drugs from the tray; FIG. 5B is a view illustrating a state in which the drug picking device is putting the picked drugs into a prescription bottle;

FIG. 6A is a view illustrating a state in which the drug bottle has been lowered by a drug bottle raising and lowering section, and the drug picking device is picking the drugs unnecessary for the prescription from the tray, and putting the drugs into the drug bottle; FIG. 6B is a view illustrating a state in which the drug bottle has been raised by the drug bottle raising and lowering section and the cap has been attached to the drug bottle again by the cap removing device; and FIG. 6C is a view illustrating a state in which the drug bottle is to be turned by the drug bottle turning section and slid toward a side opposite to the tray.

DETAILED DESCRIPTION

Figure 1A:
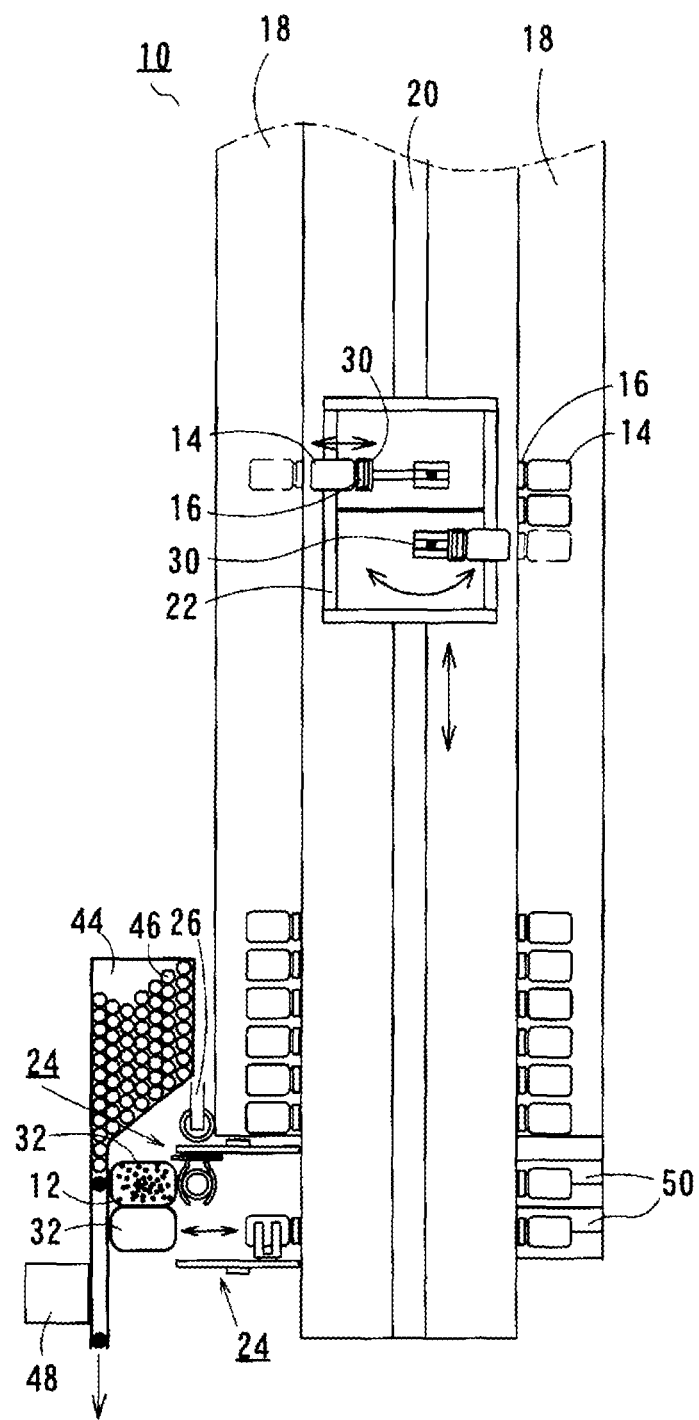
FIGS. 1A and 1B illustrate an automatic drug dispensing and picking system according to an embodiment of the present invention.
Figure 1B:
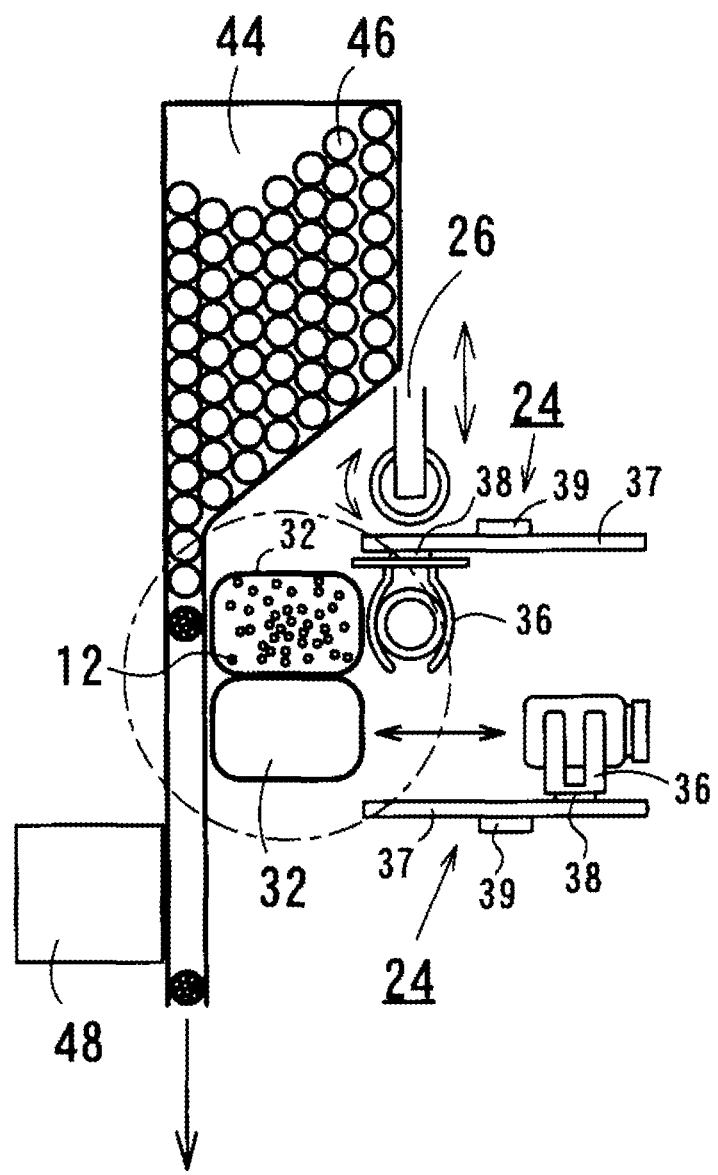
Figure 2A:
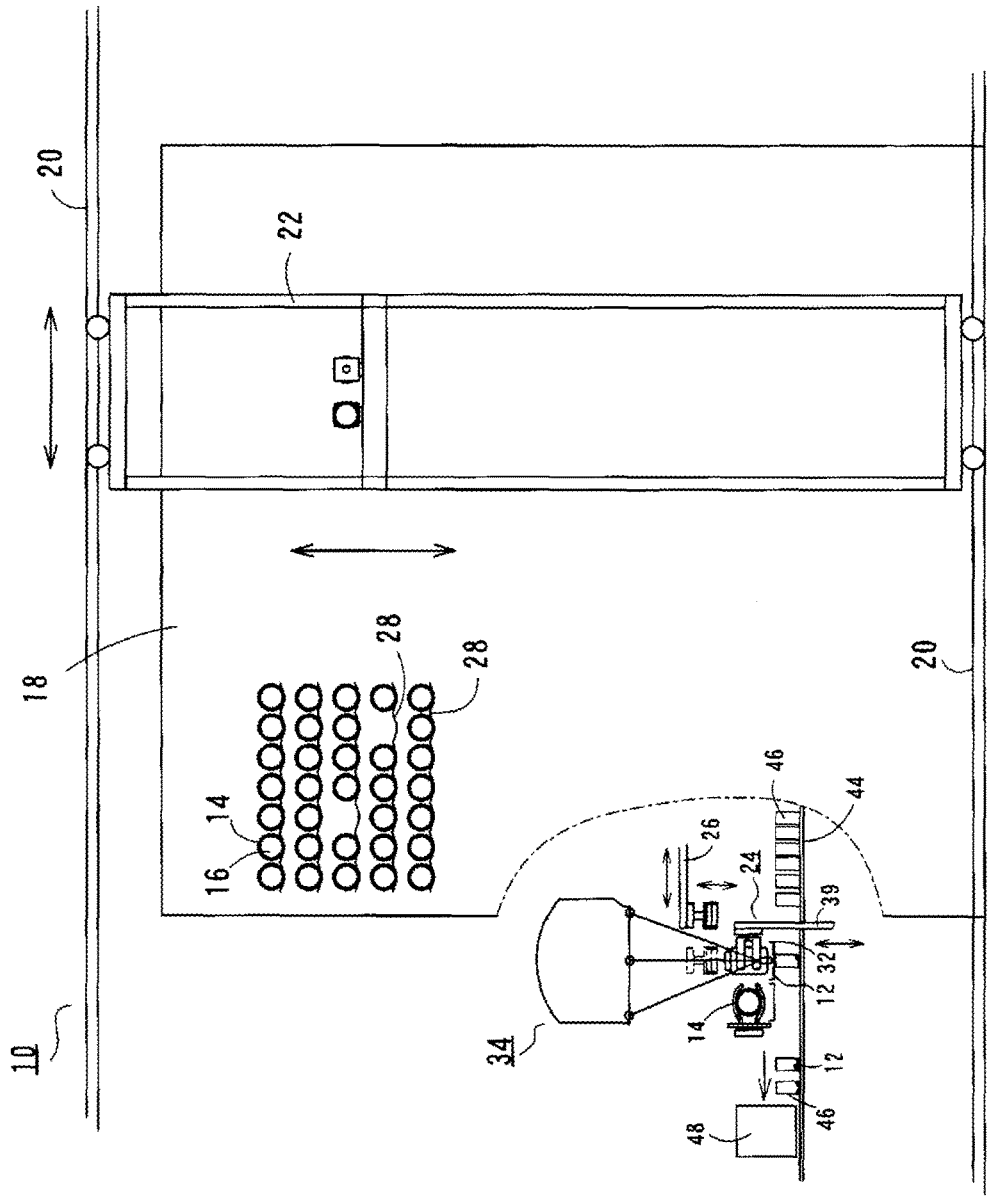
FIGS. 2A and 2B illustrate the automatic drug dispensing and picking system according to the embodiment of the present invention.
Figure 2B:
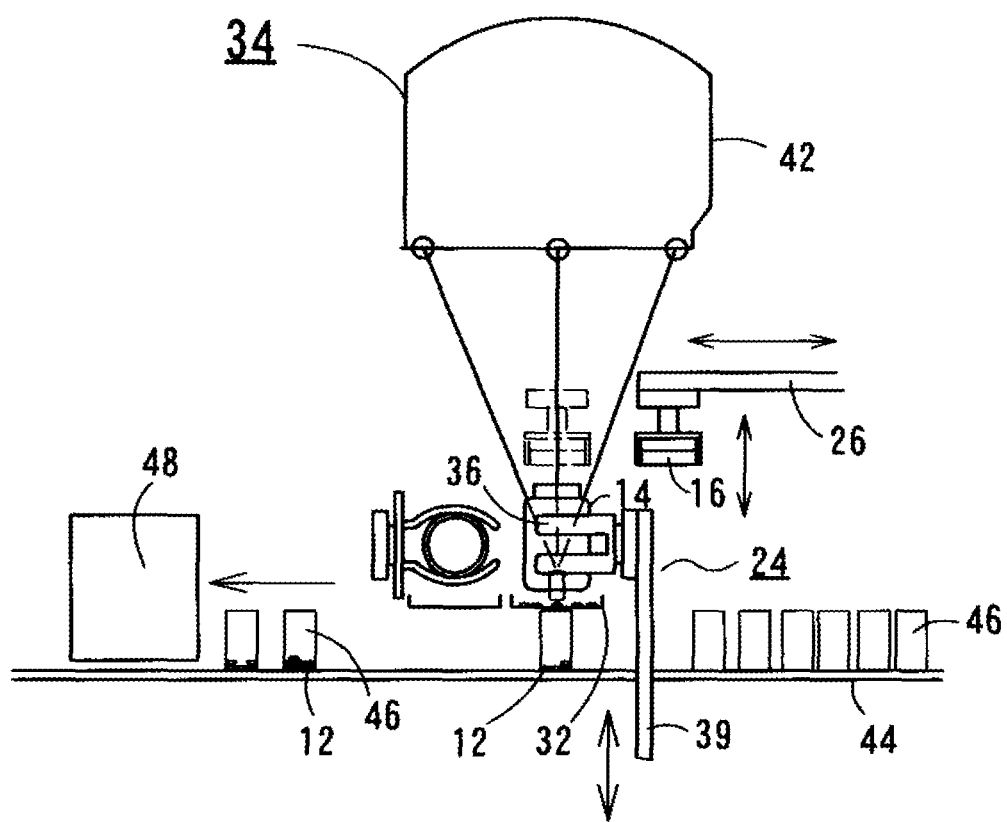
Figure 3A:
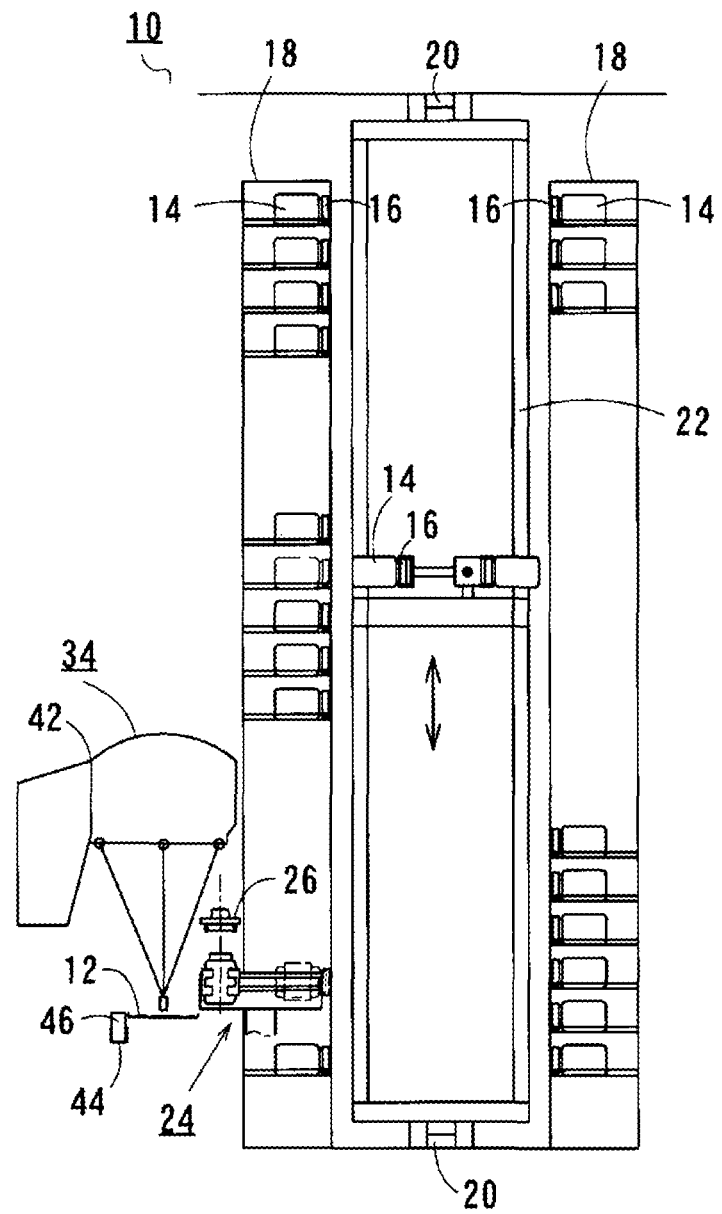
FIGS. 3A and 3B illustrate the automatic drug dispensing and picking system according to the embodiment of the present invention.
Figure 3B:
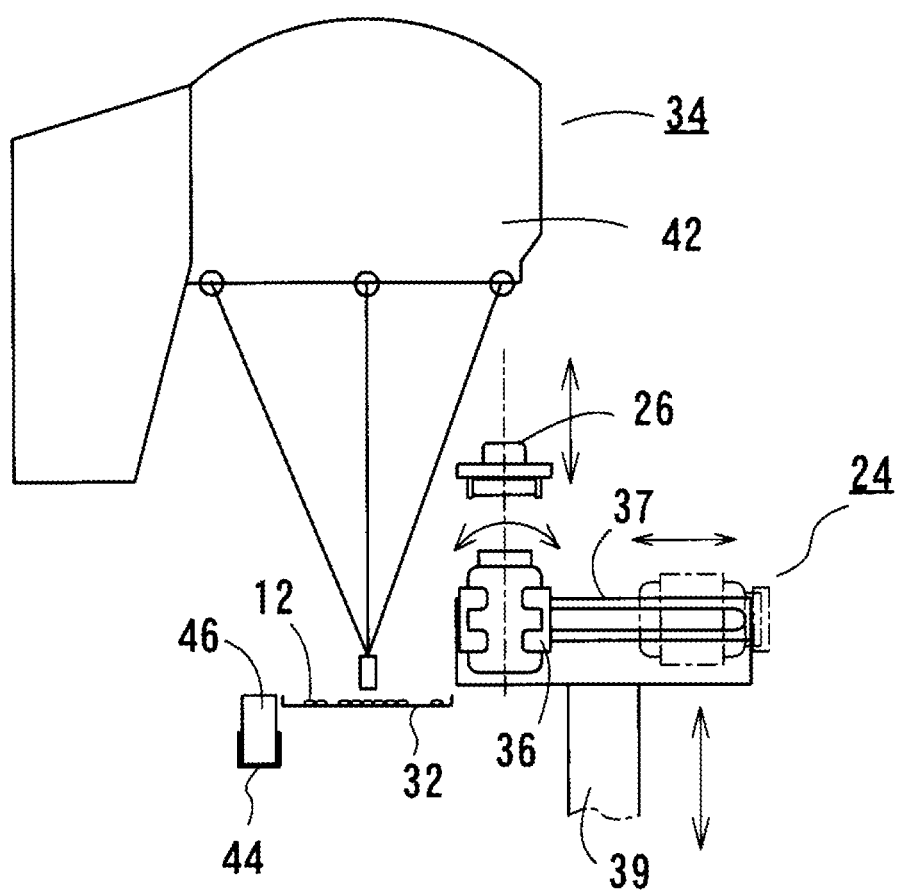

The following describes an automatic drug dispensing and picking system according to an embodiment of the present invention with reference to the drawings. FIGS. 1A and 1B illustrate the automatic drug dispensing and picking system according to the embodiment of the present invention. FIG. 1A is a schematic plan view of a configuration thereof. FIG. 1B is an enlarged schematic plan view of a configuration of a downstream portion from a drug bottle control device. FIGS. 2A and 2B illustrate the automatic drug dispensing and picking system according to the embodiment of the present invention. FIG. 2A is a schematic side view of the configuration thereof. FIG. 2B is an enlarged schematic side view of the configuration of the downstream portion from the drug bottle control device. FIGS. 3A and 3B illustrate the automatic drug dispensing and picking system according to the embodiment of the present invention. FIG. 3A is a schematic front view of the configuration thereof. FIG. 3B is an enlarged schematic front view of the configuration of the downstream portion from the drug bottle control device.

An automatic drug dispensing and picking system 10 includes a drug bottle 14 containing drugs 12 and including a cap 16 attached thereto, drug bottle storage racks 18, a traveling rail 20, a crane device 22, a drug bottle control device 24, a cap removing device 26, shelves 28 of the drug bottle storage racks 18, a picking arm 30, a tray 32, a drug picking device 34, a drug bottle holding section 36, a sliding section 37, a drug bottle turning section 38, a drug bottle raising and lowering section 39, a parallel link robot 42, a conveyance belt 44, a prescription bottle 46, a label printer 48, and a new drug bottle receiving section 50.

The automatic drug dispensing and picking system 10 according to the present embodiment is a system that automatically dispenses prescribed drugs on the basis of prescription data. As illustrated in FIGS. 1A, 1B, 2A, 2B, 3A, and 3B, the automatic drug dispensing and picking system 10 includes the drug bottle storage racks 18, the traveling rail 20, the crane device 22, the drug bottle control device 24, the cap removing device 26, and the drug picking device 34. The plurality of drug bottle storage racks 18 is arranged side by side in parallel at a predetermined interval. Each drug bottle storage rack 18 includes multiple shelves and rows, and stores a plurality of drug bottles 14 therein. Each drug bottle 14 contains drugs 12 therein and includes a cap 16 attached thereto. The traveling rail 20 is arranged between the drug bottle storage racks 18 along a width direction of the drug bottle storage racks 18. The crane device 22 travels the traveling rail 20, and picks a drug bottle 14 containing the prescribed drugs 12 from a corresponding one of the drug bottle storage racks 18 on the basis of the prescription data. The drug bottle control device 24 receives, from the crane device 22, the drug bottle 14 that the crane device 22 has picked from the drug bottle storage rack 18. From the received drug bottle 14, the drug bottle control device 24 discharges the drugs 12 contained in the drug bottle 14 to the adjacent tray 32. The cap removing device 26 removes a cap 16 attached to the drug bottle 14 that the drug bottle control device 24 has received from the crane device 22. The drug picking device 34 picks, on the basis of the prescription data, the number of drugs 12 necessary for the prescription from among the drugs 12 discharged to the tray 32 by the drug bottle control device 24. The drug picking device 34 then puts the picked drugs 12 into the prescription bottle 46 conveyed by the adjacent conveyance belt 44.

Furthermore, in the automatic drug dispensing and picking system 10 according to the present embodiment, each drug bottle 14 is laid and stored horizontally in a direction in which the cap 16 attached thereto faces the traveling rail 20. Among the drugs 12 discharged to the tray 32, drugs 12 unnecessary for the prescription are contained again into the drug bottle 14 by the drug bottle control device 24 on the basis of the prescription data. In addition, the drug bottle control device 24 passes the drug bottle 14 to the crane device 22. When the crane device 22 receives the drug bottle 14, the crane device 22 stores the drug bottle 14 in the corresponding drug bottle storage rack 18. Note that although the two drug bottle storage racks 18 are arranged side by side in parallel at the predetermined interval in the present embodiment, one drug bottle storage rack 18 or three or more drug bottle storage racks 18 may be arranged, alternatively.

The following describes in detail the automatic drug dispensing and picking system 10 according to the present embodiment. In the automatic drug dispensing and picking system 10 according to the present embodiment, each drug bottle storage rack 18 includes multiple shelves and rows, as illustrated in FIG. 2A. As illustrated in FIGS. 1A and 3A, the drug bottles 14 containing the drugs 12 are stored in each shelf 28 of the respective drug bottle storage racks 18 with the drug bottles 14 laid horizontally in the direction in which each drug bottle 14 faces the traveling rail 20 (direction in which the cap 16 thereof faces the traveling rail 20). In the present embodiment, as illustrated in FIG. 2A, each shelf 28 of the drug bottle storage racks 18 is formed in a corrugated shape, and each drug bottle 14 is laid horizontally in a trough portion of the corrugated shape. With the shelves 28 shaped in this way, the stability of the drug bottles 14 is secured.

Laying and storing the drug bottles 14 horizontally in this way helps to narrow the height space of each shelf 28 of the drug bottle storage racks 18. As a result, numerous drug bottles 14 can be stored. Furthermore, with the drug bottles 14 laid horizontally in the direction in which each drug bottle 14 faces the traveling rail 20, the picking arm 30 attached to the crane device 22 can pick each of the drug bottles 14 easily. In general, the sizes of the drug bottles 14 are different from one another. With each cap 16 facing the traveling rail 20, however, the picking arm 30 can grasp the cap 16. Therefore, there is an advantage that the picking operation is hardly affected by the shapes of the drug bottles 14.

The crane device 22 according to the present embodiment travels the traveling rail 20 arranged between the drug bottle storage racks 18 along the width direction of the drug bottle storage racks 18. The crane device 22 picks, from a corresponding one of the drug bottle storage racks 18, a drug bottle 14 containing prescribed drugs 12 on the basis of prescription data. As illustrated in FIG. 1A, the picking arm 30 is configured such that the picking arm 30 is rotatable in a horizontal direction, and expanded and contracted in the directions toward and away from the drug bottle storage racks 18.

Such a configuration, therefore, creates an excellent effect that from the corresponding one of the drug bottle storage racks 18 arranged on both sides of the traveling rail 20, the picking arm 30 can pick any of the drug bottles 14 stored in the respective drug bottle storage racks 18 at high speed. Subsequently, the crane device 22 that has picked the drug bottle 14 passes the drug bottle 14 to the drug bottle control device 24, as illustrated in FIGS. 1A, 1B, and 4A to 4E.

Subsequently, as illustrated in FIGS. 4A to 4E, the drug bottle control device 24 according to the present embodiment receives, from the crane device 22, the drug bottle 14 that the crane device 22 has picked from the corresponding drug bottle storage rack 18. The drug bottle control device 24 then discharges, from the received drug bottle 14, the drugs 12 contained therein to the adjacent tray 32.

Figure 4A:
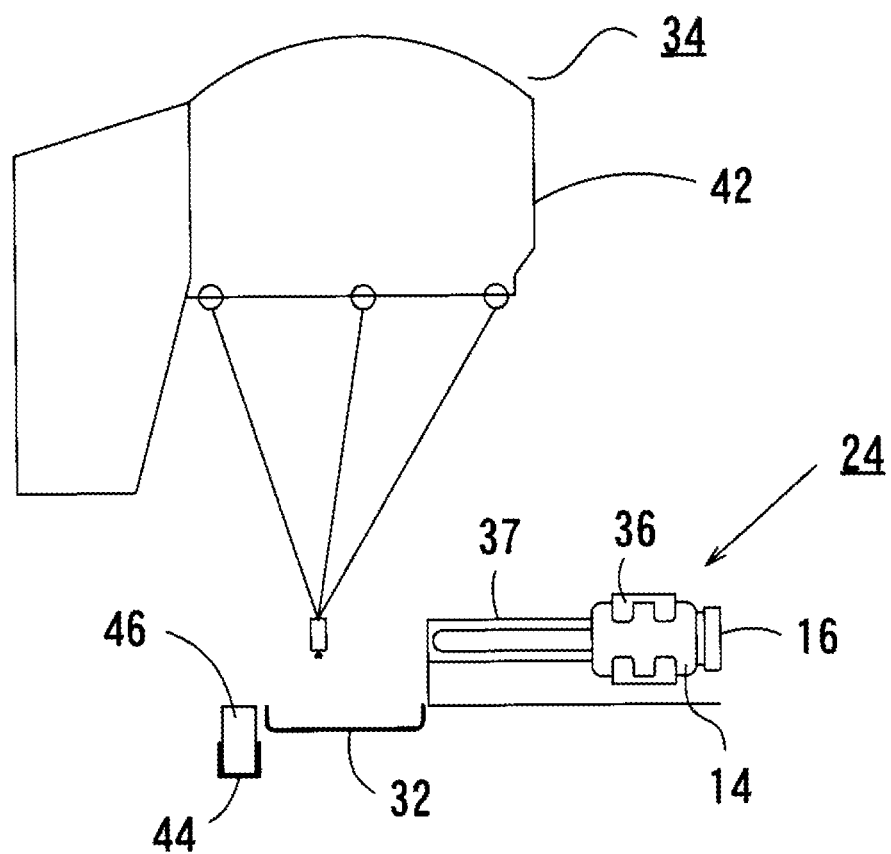
FIGS. 4A to 4E are schematic views illustrating, from a front side, a flow of operations of the drug bottle control device and a cap removing device in the automatic drug dispensing and picking system according to the embodiment of the present invention.
Figure 4B:
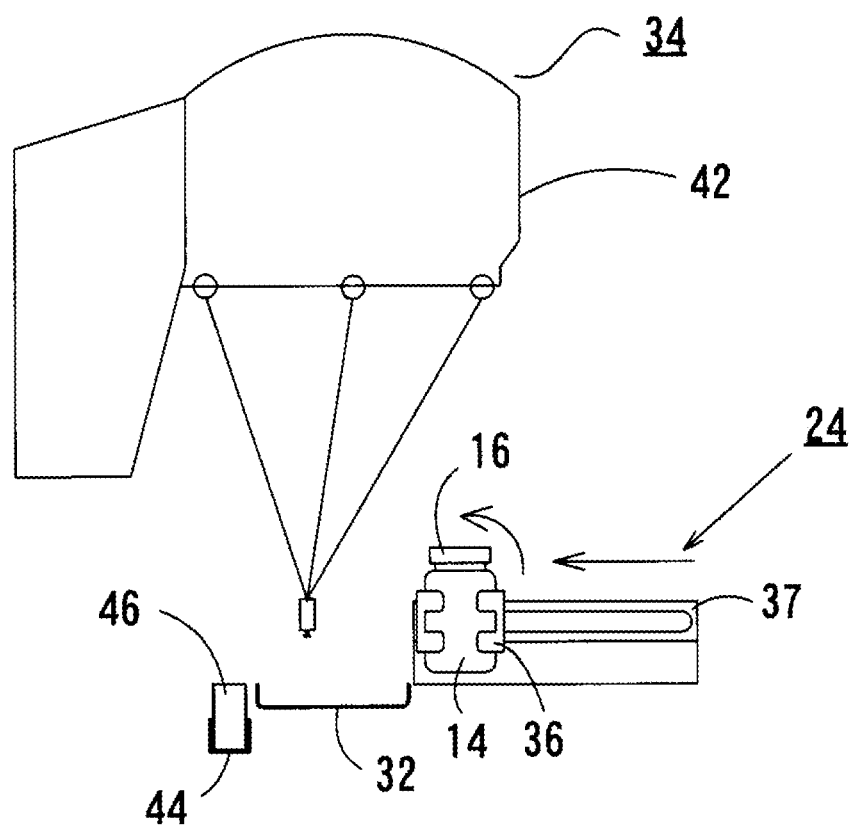

The following describes the operations of the drug bottle control device 24 according to the present embodiment. As illustrated in FIG. 4A, the drug bottle holding section 36 in the drug bottle control device 24 grasps and holds the drug bottle 14 received from the crane device 22. Subsequently, as illustrated in FIG. 4B, the drug bottle holding section 36 is slid toward the tray 32 by the sliding section 37 while grasping the drug bottle 14. The drug bottle turning section 38 then vertically turns the drug bottle holding section 36 such that the cap 16 faces upward.

Figure 4C:
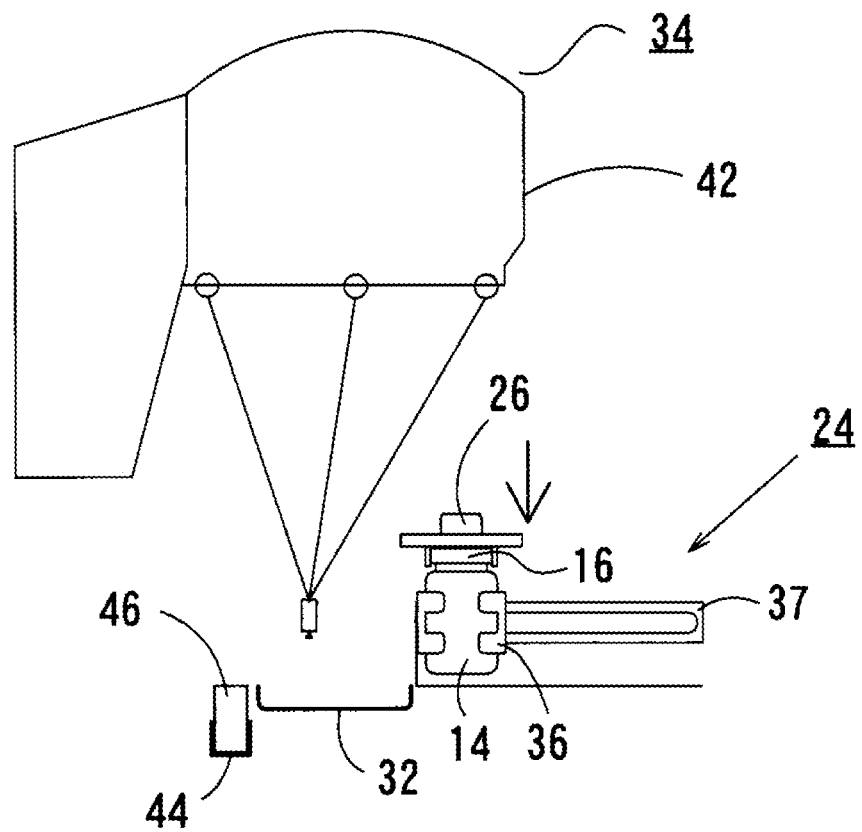
Figure 4D:
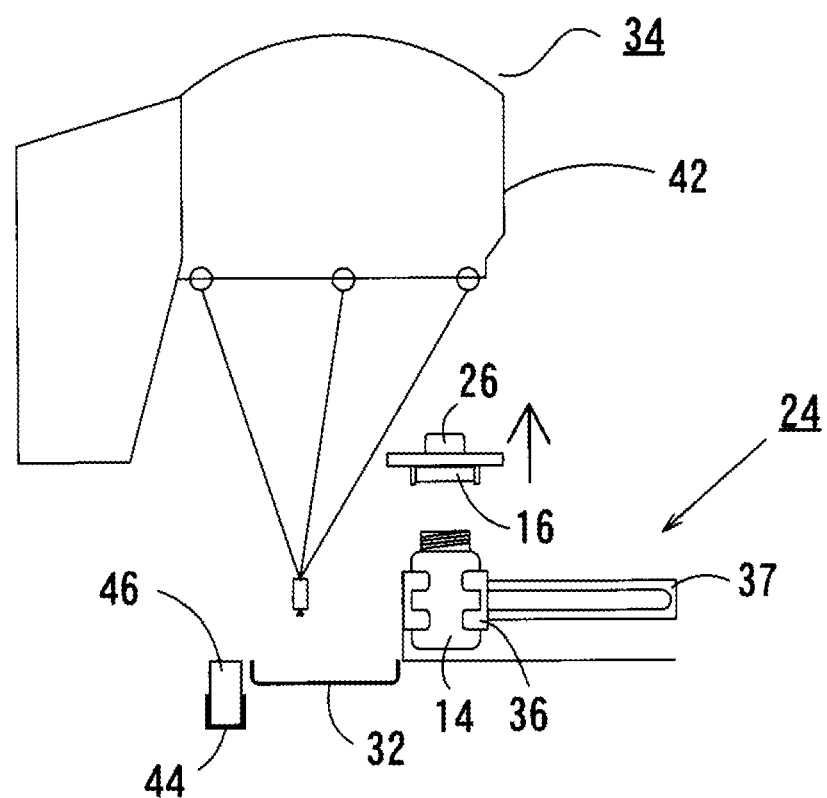
Figure 4E:
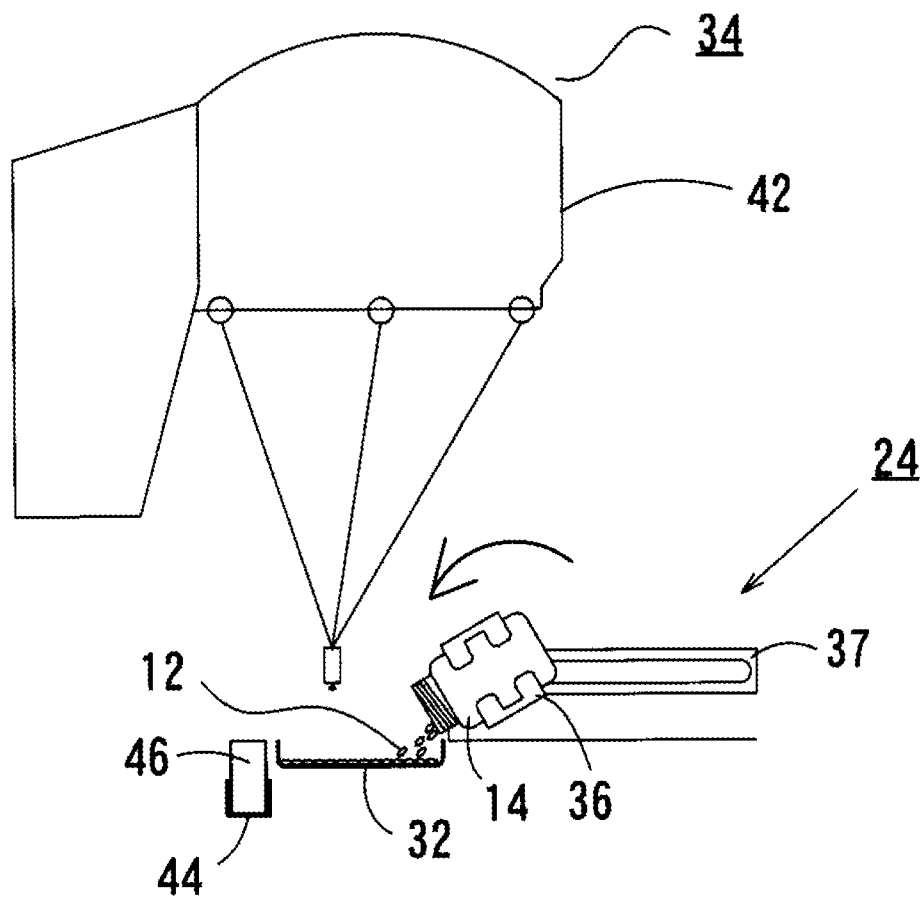

As illustrated in FIGS. 4C and 4D, the cap removing device 26 removes the cap 16 of the drug bottle 14 from the drug bottle 14 by grasping and rotating the cap 16 thereof. In this way, an opening portion of the drug bottle 14 is exposed. As illustrated in FIG. 4E, the drug bottle turning section 38 vertically turns the drug bottle holding section 36 at a predetermined angle, and discharges the drugs 12 contained in the drug bottle 14 to the tray 32. Preferably, the drugs 12 are discharged in a smooth manner by using, for example, a mechanism that vibrates the drug bottle holding section 36.

Figure 5A:
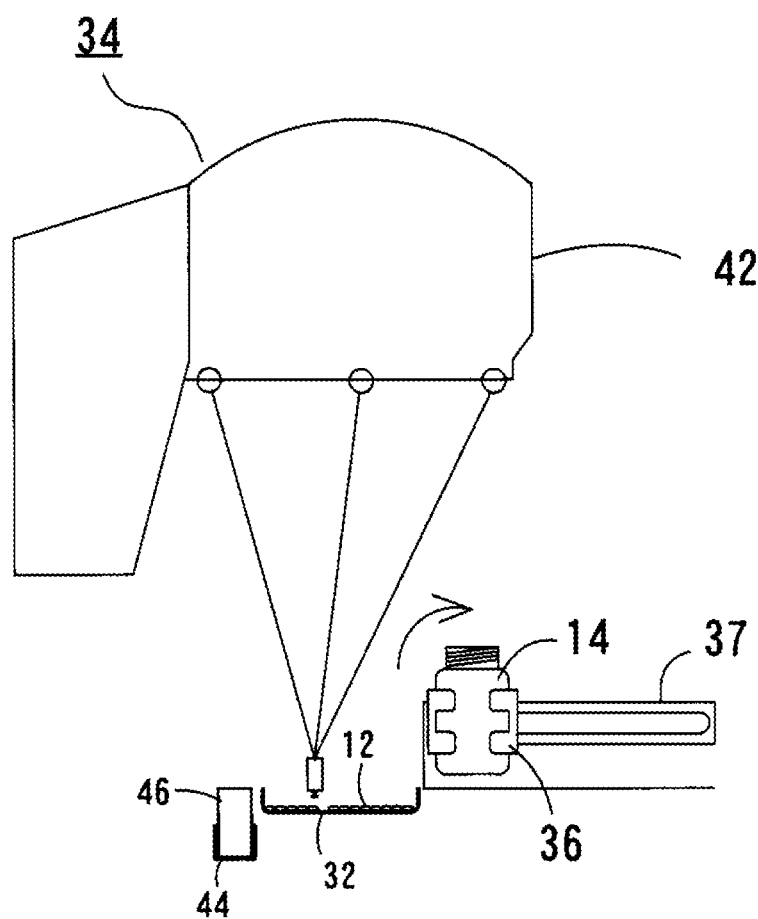
FIGS. 5A and 5B are schematic views illustrating, from the front side, a flow of operations of a drug picking device in the automatic drug dispensing and picking system according to the embodiment of the present invention.

The following describes the operations of the drug picking device 34 picking the drugs 12 discharged to the tray 32. As illustrated in FIG. 5A, the drug picking device 34 causes a camera or the like (not illustrated) mounted therein to identify, among the drugs 12 discharged to the tray 32, the number of drugs 12 necessary for the prescription on the basis of the prescription data. The drug picking device 34 also causes the parallel link robot 42 to pick, at high speed, the identified drugs 12 by suction or the like. At this time, the drug bottle turning section 38 vertically turns the drug bottle holding section 36 such that the opening portion of the drug bottle 14 faces upward.

Figure 5B:
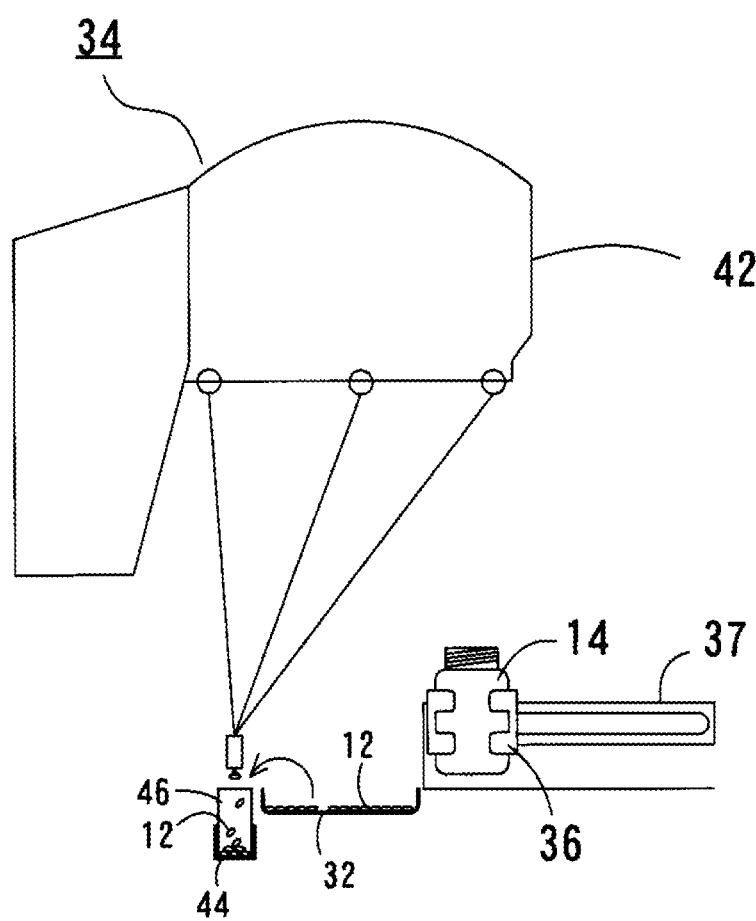

Then, as illustrated in FIG. 5B, the parallel link robot 42 puts the picked drugs 12 into a prescription bottle 46 conveyed by the adjacent conveyance belt 44. Subsequently, the prescription bottle 46 into which the drugs 12 have been put is conveyed toward the downstream side of the conveyance belt 44. A label describing information necessary for the prescription, which is created by the label printer 48, is then attached to the prescription bottle 46. After that, the prescription bottle 46 is subjected to a final inspection.

Figure 6A:
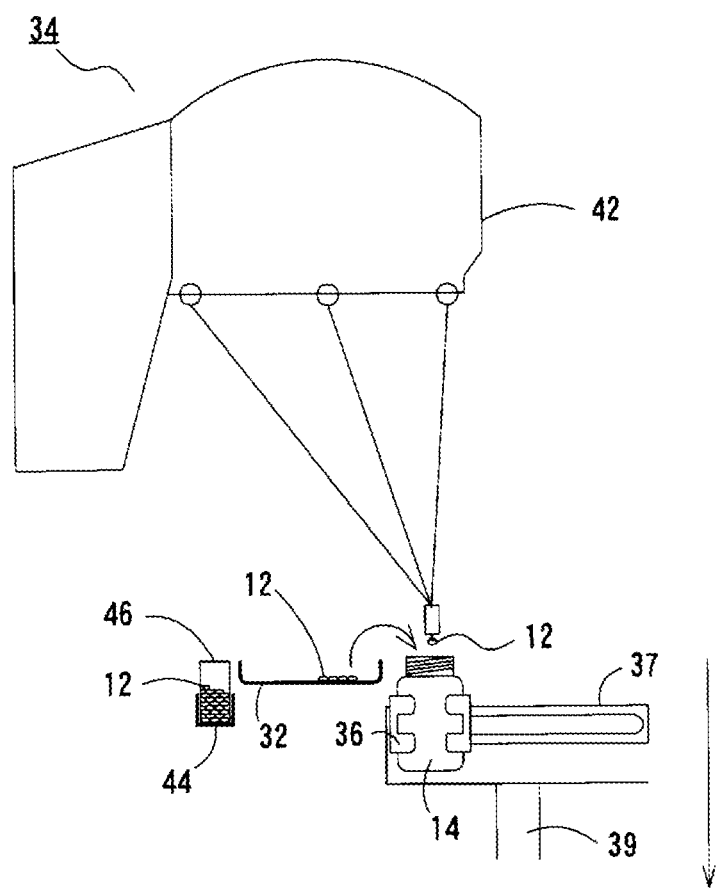
FIGS. 6A to 6C are schematic views illustrating, from the front side, a flow of operations of returning, to the drug bottle, drugs unnecessary for prescription in the automatic drug dispensing and picking system according to the embodiment of the present invention.

The following describes the operations of containing drugs 12 unnecessary for the prescription again in the drug bottle 14, among the drugs 12 discharged to the tray 32. As illustrated in FIG. 6A, the drug bottle turning section 38 vertically turns the drug bottle holding section 36 such that the opening portion of the drug bottle 14 faces upward. Then, the drug bottle raising and lowering section 39 lowers the sliding section 37 together with the drug bottle holding section 36 until the opening portion of the drug bottle 14 is in a position near the height of the tray 32.

Subsequently, the drug picking device 34 puts the drugs 12 unnecessary for the prescription from the tray 32 into the opening portion of the drug bottle 14. In the present embodiment, the drugs 12 are identified by the camera or the like (not illustrated) mounted in the drug picking device 34, and the identified drugs 12 are picked by the parallel link robot 42 (such as by suction) and put into the opening portion of the drug bottle 14.

Figure 6B:
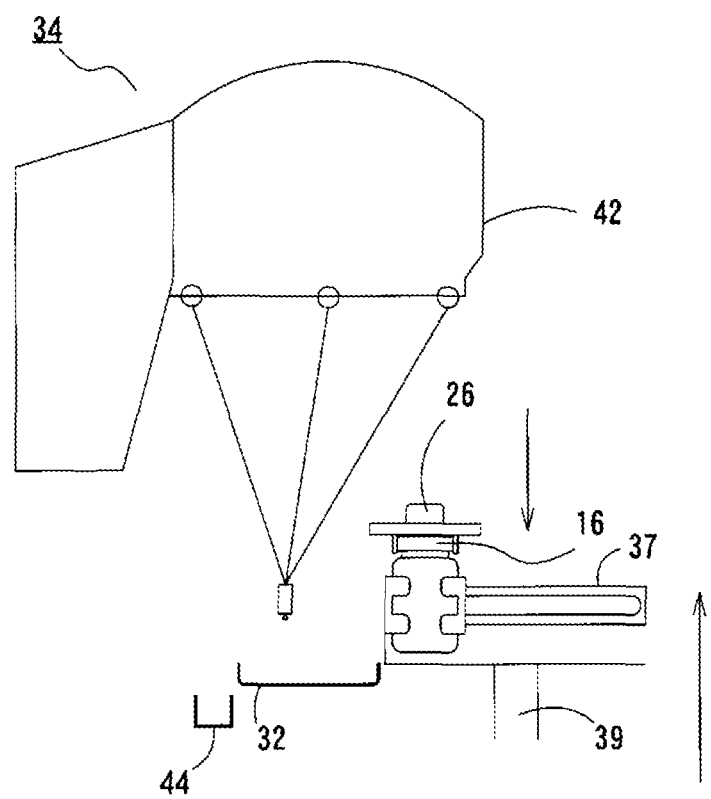

Then, as illustrated in FIG. 6B, the drug bottle raising and lowering section 39 raises the sliding section 37 together with the drug bottle holding section 36 until the drug bottle 14 is in an initial height position. Then, the cap removing device 26 attaches the cap 16 to the drug bottle 14 again.

Figure 6C:
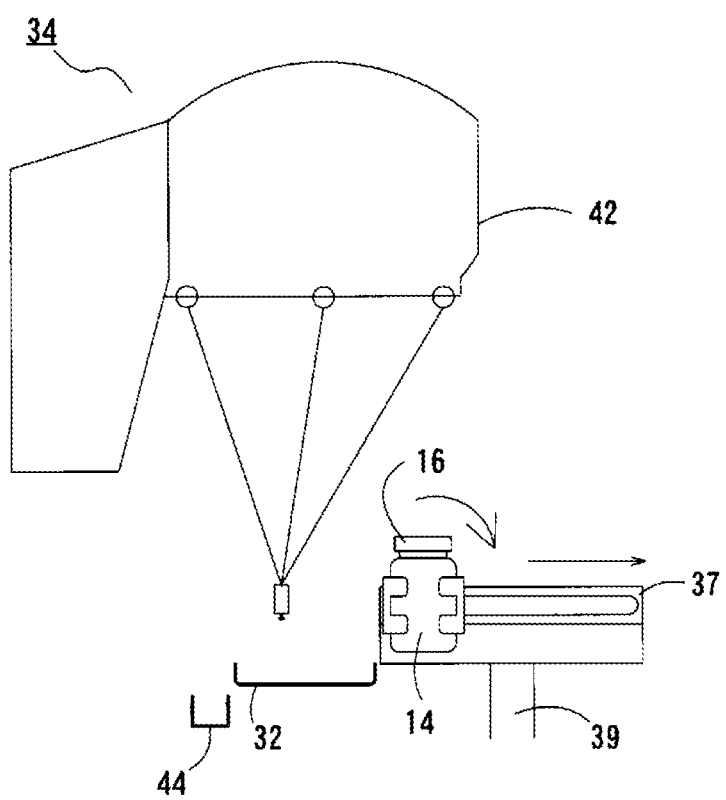

Subsequently, as illustrated in FIG. 6C, the drug bottle turning section 38 turns the drug bottle holding section 36 vertically in the direction in which the cap 16 attached to the drug bottle 14 faces the traveling rail 20. Then, the sliding section 37 slides the drug bottle holding section 36 toward the traveling rail 20. Alternatively, each of the drug bottle control device 24, the cap removing device 26, and the tray 32 may be arranged in pairs. With such a configuration, a series of operations from the operations of the drug bottle control device 24 to the operation of containing the drugs 12 unnecessary for the prescription again in the drug bottle 14 can be alternately performed in parallel. As a result, it is possible to speed up the dispensing work further.

The following describes the operations when the drug bottle 14 into which the drugs 12 are contained again is stored in the corresponding drug bottle storage rack 18. When the drug bottle holding section 36 is detached from the drug bottle 14, the crane device 22 receives the drug bottle 14 by causing the picking arm 30 to grasp the cap 16 of the drug bottle 14. Subsequently, while maintaining the state of the received drug bottle 14 laid horizontally, the crane device 22 stores the received drug bottle 14 in the corresponding one of the drug bottle storage racks 18 arranged on both sides of the crane device 22.

In the present embodiment, as illustrated in FIG. 1A, the new drug bottle receiving section 50 is arranged on a side opposite to the drug bottle control device 24 with the traveling rail 20 interposed therebetween. The new drug bottle receiving section 50 passes a newly received drug bottle 14 to the crane device 22. In passing the drug bottle 14 to the crane device 22, the drug bottle 14 is placed in the new drug bottle receiving section 50 with the drug bottle 14 laid horizontally in the direction in which the cap 16 faces the traveling rail 20.

Subsequently, the crane device 22 causes the picking arm 30 to grasp and pick the cap 16 of the drug bottle 14. The picking arm 30 then stores the drug bottle 14 in a corresponding one of the drug bottle storage racks 18 arranged on both sides of the crane device 22 while maintaining the state of the drug bottle 14 laid horizontally. With such a system, the series of operations from dispensing to reception of drugs 12 can be performed at high speed.

The invention claimed is:

1. An automatic drug dispensing and picking system that automatically dispenses prescribed drugs on the basis of prescription data, the automatic drug dispensing and picking system comprising:
   a plurality of drug bottle storage racks arranged side by side in parallel at a predetermined interval, each drug bottle storage rack including multiple shelves and rows and storing a plurality of drug bottles, each drug bottle containing drugs therein and including a cap attached thereto;

a traveling rail arranged between, and along a width direction of, the drug bottle storage racks arranged side by side;

a crane device configured to travel the traveling rail and pick, on the basis of the prescription data, a drug bottle containing the prescribed drugs from a corresponding one of the drug bottle storage racks;

a drug bottle control device configured to receive, from the crane device, the drug bottle that the crane device has picked from the corresponding drug bottle storage rack, and discharge, from the received drug bottle, the drugs contained therein to an adjacent tray;

a cap removing device configured to remove a cap attached to the drug bottle that the drug bottle control device has received from the crane device; and a drug picking device configured to pick, from among the drugs discharged to the tray by the drug bottle control device, the number of drugs necessary for prescription on the basis of the prescription data, and put the picked drugs into a prescription bottle conveyed by an adjacent conveyance belt, wherein each drug bottle is stored in the corresponding drug bottle storage rack with each drug bottle laid horizontally in a direction in which the cap attached thereto faces the traveling rail, the crane device includes a picking arm attached thereto and configured to be driven to rotate in a horizontal direction, and causes the picking arm to grasp the cap of the drug bottle to pick the drug bottle from the corresponding one of the drug bottle storage racks arranged on both sides of the crane device, and then pass the drug bottle to the drug bottle control device, while maintaining the state of the drug bottle laid horizontally, the drug bottle control device includes a drug bottle holding section configured to grasp and hold, from an outside of the drug bottle, the drug bottle received from the crane device, a sliding section capable of sliding the drug bottle holding section toward and away from the tray, a drug bottle turning section configured to turn the drug bottle holding section vertically at a predetermined angle, and a drug bottle raising and lowering section configured to raise and lower the drug bottle holding section within a predetermined height range, in discharging the drugs contained in the drug bottle to the tray, the sliding section slides, toward the tray, the drug bottle holding section grasping the drug bottle received from the crane device, the drug bottle turning section vertically turns the drug bottle holding section such that the cap attached to the drug bottle faces upward, the cap removing device removes the cap attached to the drug bottle to expose an opening portion of the drug bottle, the drug bottle turning section discharges the drugs contained in the drug bottle to the tray by turning the drug bottle holding section vertically at the predetermined angle, and the drug bottle turning section vertically turns the drug bottle holding section such that the opening portion of the drug bottle faces upward, in containing, among the drugs discharged to the tray, drugs unnecessary for the prescription again in the drug bottle, the drug bottle raising and lowering section lowers the sliding section until the opening portion of the drug bottle is in a position near a height of the tray, the drug picking device puts the drugs unnecessary for the prescription from the tray into the opening portion of the drug bottle, the drug bottle raising and lowering section raises the sliding section until the drug bottle is in an initial height position, the cap removing device attaches the cap to the drug bottle again, the drug bottle turning section turns the drug bottle holding section vertically in the direction in which the cap attached to the drug bottle faces the traveling rail, and the sliding section slides the drug bottle holding section toward the traveling rail, and in storing the drug bottle in the corresponding drug bottle storage rack again, the drug bottle control device detaches the drug bottle holding section from the drug bottle and passes the drug bottle to the crane device, and the crane device stores, upon receiving the drug bottle from the drug bottle control device, the drug bottle in the corresponding one of the drug bottle storage racks arranged on both sides of the crane device by causing the picking arm to grasp the cap of the drug bottle while maintaining the state of the drug bottle laid horizontally.

2. The automatic drug dispensing and picking system, according to claim 1, wherein the drug picking device includes a drug identification sensor capable of identifying the drugs and a parallel link robot configured to pick the drugs and including a plurality of link mechanisms combined in parallel, in picking the number of drugs necessary for the prescription on the basis of the prescription data from among the drugs discharged to the tray by the drug bottle control device and putting the picked drugs into the prescription bottle conveyed by the adjacent conveyance belt, the drug picking device picks the number of drugs necessary for the prescription and puts the picked drugs into the prescription bottle by causing the drug identification sensor to identify the number of drugs necessary for the prescription among the drugs discharged to the tray, and causing the parallel link robot to pick the identified drugs, and in containing the drugs unnecessary for the prescription again in the drug bottle among the drugs discharged to the tray, the drug picking device puts the picked drugs into the drug bottle by causing the drug identification sensor to identify the drugs unnecessary for the prescription among the drugs discharged to the tray, and causing the parallel link robot to pick the identified drugs.

3. The automatic drug dispensing and picking system according to claim 1, wherein the drug bottle control device is arranged in pairs side by side, and the cap removing device and the tray adjacent to the drug bottle control device are each arranged in pairs side by side to correspond to the drug bottle control device.

4. The automatic drug dispensing and picking system according to claim 1, wherein each shelf of the drug bottle storage racks is formed in a corrugated shape, and each drug bottle is stored in a trough portion of the corrugated shape.

5. The automatic drug dispensing and picking system according to claim 1, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

6. The automatic drug dispensing and picking system according to claim 2,
wherein the drug bottle control device is arranged in pairs side by side, and the cap removing device and the tray adjacent to the drug bottle control device are each arranged in pairs side by side to correspond to the drug bottle control device.

7. The automatic drug dispensing and picking system according to claim 2,
wherein each shelf of the drug bottle storage racks is formed in a corrugated shape, and each drug bottle is stored in a trough portion of the corrugated shape.

8. The automatic drug dispensing and picking system according to claim 3,
wherein each shelf of the drug bottle storage racks is formed in a corrugated shape, and each drug bottle is stored in a trough portion of the corrugated shape.

9. The automatic drug dispensing and picking system according to claim 6,
wherein each shelf of the drug bottle storage racks is formed in a corrugated shape, and each drug bottle is stored in a trough portion of the corrugated shape.

10. The automatic drug dispensing and picking system according to claim 2, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

11. The automatic drug dispensing and picking system according to claim 3, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

12. The automatic drug dispensing and picking system according to claim 6, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

13. The automatic drug dispensing and picking system according to claim 7, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

14. The automatic drug dispensing and picking system according to claim 8, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

15. The automatic drug dispensing and picking system according to claim 9, further comprising:
a new drug bottle receiving section arranged on a side opposite to the drug bottle control device with the traveling rail interposed therebetween,
wherein with a drug bottle laid horizontally in the direction in which the cap thereof faces the traveling rail in the new drug bottle receiving section, the crane device picks the drug bottle from the new drug bottle receiving section and stores the drug bottle in a predetermined position of the corresponding drug bottle storage rack.

\* \* \* \* \*